(12) United States Patent
van den Engh

(10) Patent No.: US 7,728,974 B2
(45) Date of Patent: Jun. 1, 2010

(54) ENHANCED DETECTION SYSTEM AND METHOD

(75) Inventor: Gerrit van den Engh, Seattle, WA (US)

(73) Assignee: Cytopeia, Inc., Seattle, WA (US)

(*) Notice: Subject to any disclaimer, the term of this patent is extended or adjusted under 35 U.S.C. 154(b) by 67 days.

(21) Appl. No.: 12/027,961

(22) Filed: Feb. 7, 2008

(65) Prior Publication Data

US 2008/0186479 A1    Aug. 7, 2008

Related U.S. Application Data

(60) Provisional application No. 60/888,706, filed on Feb. 7, 2007.

(51) Int. Cl.
*G01N 21/00* (2006.01)
(52) U.S. Cl. ........................ 356/338; 356/121; 356/127; 356/600; 356/624; 348/199; 353/7
(58) Field of Classification Search ......... 356/600–624, 356/121–127; 359/346, 721, 744
See application file for complete search history.

(56) References Cited

U.S. PATENT DOCUMENTS

| | | | | |
|---|---|---|---|---|
| 2,037,014 A | * | 4/1936 | Eitzen | 353/50 |
| 2,072,478 A | * | 3/1937 | Gray | 348/199 |
| 3,482,107 A | * | 12/1969 | Fromund | 250/237 R |
| 4,813,031 A | | 3/1989 | Bierhoff | |
| 5,133,602 A | * | 7/1992 | Batchelder et al. | 356/615 |
| 5,350,695 A | * | 9/1994 | Colella et al. | 436/63 |
| 5,353,073 A | * | 10/1994 | Kobayashi | 351/221 |
| 5,760,900 A | * | 6/1998 | Ito et al. | 356/338 |
| 5,844,685 A | * | 12/1998 | Gontin | 356/433 |
| 6,982,785 B2 | | 1/2006 | Van den Engh | |
| 7,410,809 B2 | | 8/2008 | Goix et al. | |
| 2001/0024280 A1 | * | 9/2001 | Fukuda et al. | 356/609 |

* cited by examiner

*Primary Examiner*—Tarifur R. Chowdhury
*Assistant Examiner*—Isiaka O Akanbi
(74) *Attorney, Agent, or Firm*—Douglas A. Petry

(57) ABSTRACT

An enhanced detection system can eliminate use of a sheath fluid by selecting which particles that pass through an sensing region to detect parametric characteristics thereof based upon position of each particle while it is in a sensing region relative to one or more predetermined positions, such as an in-focus position relative to one or more light beams directed into the sensing region, to enhance accuracy and robustness of particle parametric characteristics detection.

5 Claims, 5 Drawing Sheets

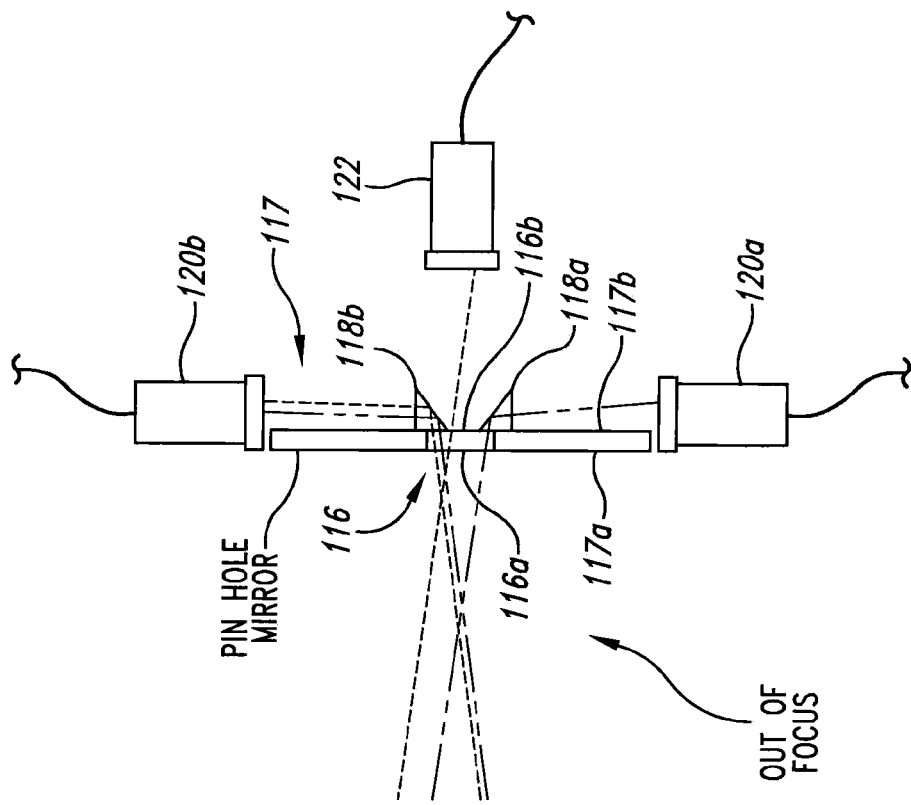
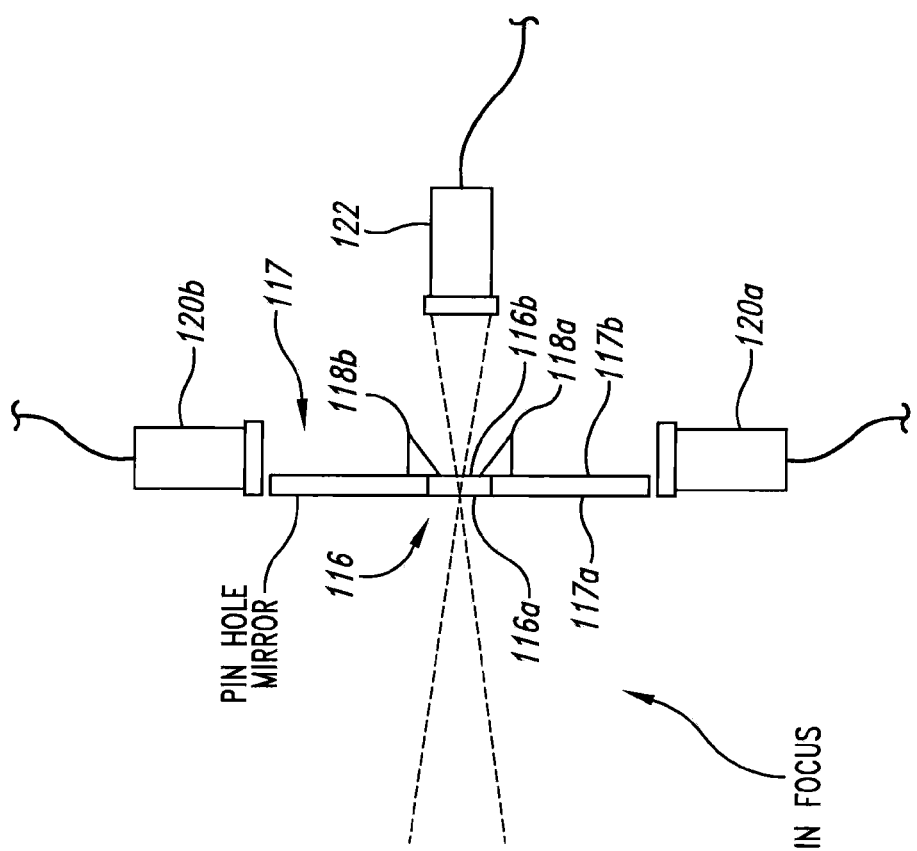

ENHANCED DETECTION SYSTEM AND METHOD

CROSS REFERENCE TO RELATED APPLICATION

This application claims priority benefit of provisional application Ser. No. 60/888,706 filed Feb. 7, 2007, the content of which is incorporated in its entirety.

FIELD OF THE INVENTION

Generally, the present invention relates to flow cytometry.

BACKGROUND OF THE INVENTION

With conventional flow cytometers, particles, such as cells, are aligned and carried along ideally in a single file arrangement within a stream of clear fluid, also known as a sheath fluid, to pass before one or more beams of light in an sensing region for subsequent detection of various parametric characteristics to classify, categorize, quantify or otherwise detect one or more aspects of the particles. This sheath fluid guides the particles substantially along a desired trajectory to keep the particles in-focus in the sensing region relative to one or more beams of light for subsequent sensing by detectors and automated quantification of cells according to predetermined parametric characteristics. Without the sheath fluid, particles while in the sensing region may not be in a proper in-focus position relative to the beams of light directed into the sensing region so that detection data would be collected regarding out-of-focus and in-focus particles. The detection data collected regarding the out-of-focus particles would lack accuracy and consequently harm the overall integrity of the data collected.

Due to the single-file nature of the particles passing in the sheath fluid, for each particle passing through or in the vicinity of one or more of the light beams in an sensing region, there is generally little or no surrounding particles so that there is little background light scatter or fluorescence to interfere with detection of the predetermined one or more parametric characteristics associated with the particle so that each of the particles can be considered as in-focus while in the sensing region with respect to the one or more beams of light involved. Unfortunately, the need for both clean sheath fluid and a highly stable stream greatly complicates the fluidics of these systems. As a consequence, setup and maintenance of these systems while measurements are being performed is very labor intensive. In addition, related system design such as involving sheath fluid management and sample injection constitute a significant proportion of the complexity found with conventional flow cytometry systems.

BRIEF DESCRIPTION OF THE SEVERAL VIEWS OF THE DRAWINGS

FIG. 3A is a side elevational schematic view of an in-focus case of an implementation of the detection system of FIG. 1 in operation.

FIG. 3B is a side elevational schematic view of an out-of-focus case of an implementation of the detection system of FIG. 1 in operation.

DETAILED DESCRIPTION OF THE INVENTION

Figure 1:
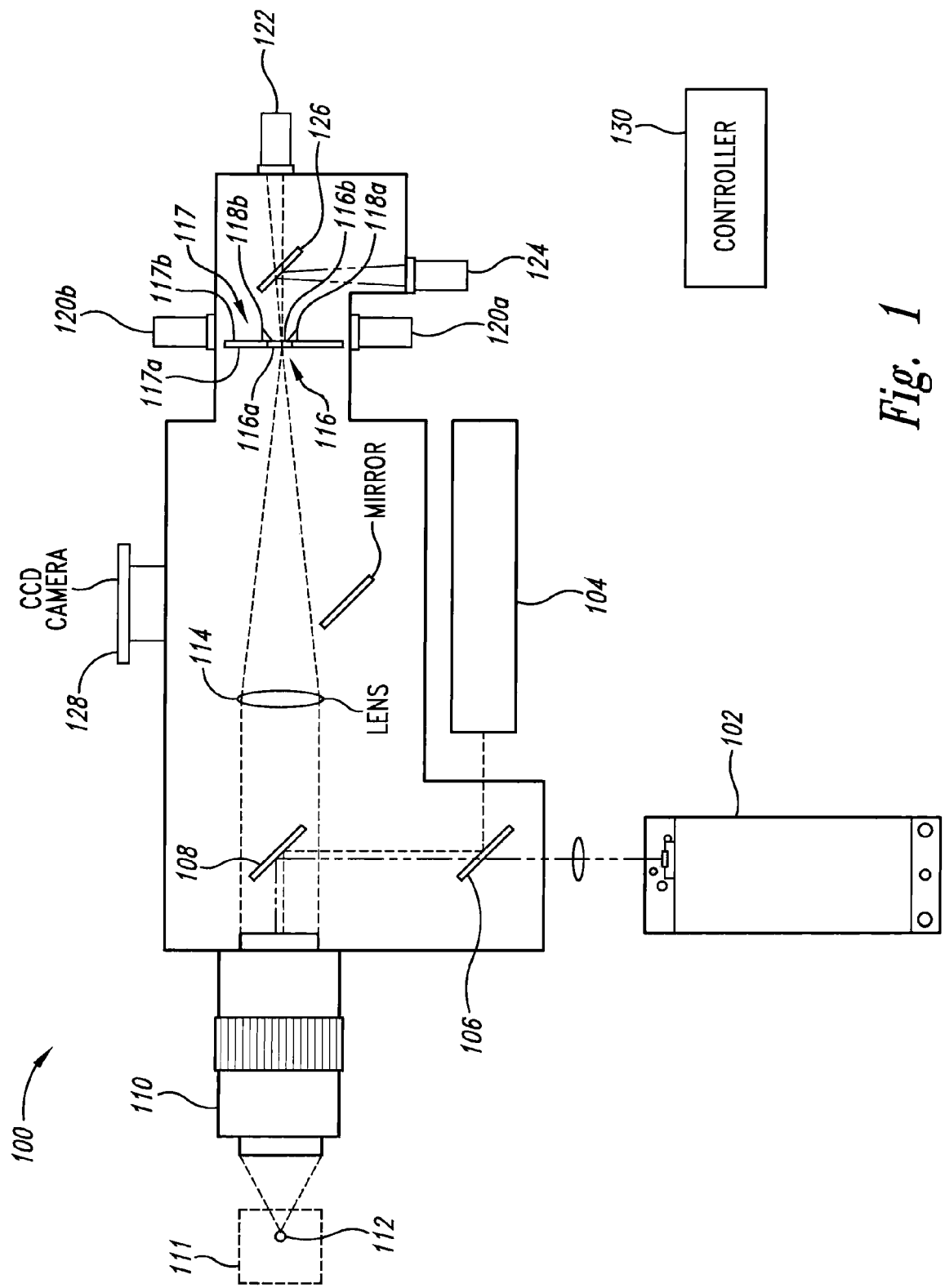
FIG. 1 is a schematic diagram of an enhanced detection system according to the present invention.

An enhanced particle parametric characteristics detection system and method has various implementations that reduce or eliminate conventional reliance on a sheath fluid. The enhanced detection system selects which particles that pass through an sensing region to detect parametric characteristics thereof based upon position of each particle while it is in the sensing region relative to one or more predetermined positions, such as an in-focus position relative to one or more light beams directed into the sensing region, to enhance accuracy and robustness of particle parametric characteristics detection. Through use of position detection while each particle is in the sensing region, the enhanced detection system can sense when a particular particle is in-focus or out-of-focus relative to the light beams directed into the sensing region used to detect predetermined characteristics of the particles. Detection data regarding in-focus particles and out-of-focus particles can be then discriminated. For instance, detection data regarding in-focus particles can then be saved and the detection data regarding out-of-focus particles can be disregarded. It can be desirable to disregard detection data for out-of-focus particles since particle positioning does not allow for accurate collection of data regarding these out-of-focus particles.

In other words, particle position information can be used to modify or disregard detection of one or more predetermined parametric characteristics associated with particles that do not follow a desired trajectory or one of a collection of trajectories while in an sensing region. In some implementations, particle position signals generated through electronic circuitry are inputted to software-based filtering to disregard detection of one or more predetermined parametric characteristics for particles that do not follow a predetermined trajectory and/or one of a collection of trajectories while in the sensing region. As a consequence, in these implementations, detectors are used to detect results caused by one or more beams of light being directed onto only those particles of a flow of particles that are in a designated position while in the sensing region, such as a position of in-focus relative to those one or more beams of light.

In some implementations, the presence of a properly positioned particle, such as an in-focus particle, having a predetermined trajectory while in an observation can be ascertained with a sensing system based upon confocal microscopy. Other implementations can use other ways to determine which particles in a flow of particles occupy a predetermined position, such as an in-focus position, while in a sensing region. Confocal microscopy teaches that images related to properly positioned particles, such as in-focus particles, will be focused to pass through an aperture, such as a pinhole mirror, which can then be received by a single selectively positioned detector, while images related to improperly positioned particles, such as out-of-focus particles, will be unfocused thereby casting light in a plurality of directions that can then be detected by appropriately placed detectors. Signals sent from the detectors can then be analyzed to ascertain status regarding whether each particle in a flow of particles is positioned while in a sensing region either in an in-focus position or an out-of-focus position.

Implementations of the enhanced detection system can be operated without need of a sheath fluid and thus can be used to directly analyze environmental samples such as ocean, lake, and stream water. The enhanced detection system provides an added convenience with compactness, few moving parts, relatively low power requirements, and ease of operation that can be exploited in many applications such as found with use in remote locations and unattended operation. Another aspect of the enhanced detection system is that the technique may be extended to incorporate other cytometric measurements involving additional lasers, scattering, apertures, fluorescence bands, and/or polarization measurements.

An exemplary enhanced detection system 100 is depicted in FIG. 1 as having a first laser 102 of a first wavelength (e.g. 532 nm) and a second laser 104 of a second wavelength (e.g. 638 nm). The enhanced detection system 100 includes a dichroic mirror 106 (selectively passes light of the first wavelength and reflects light of the second wavelength), a prism (or mirror or other reflector) 108 and a microscope objective 110 (uses confocal illumination) to produce two (nearly) co-linear laser lines to illuminate a sensing region 111 shown as containing an in-focus particle 112.

The enhanced detection system 100 includes a lens 114 to focus light from the objective 110 that has impinged upon material in the sensing region 111, such as the in-focus particle 112. The focus light is directed to an aperture 116 (with a proximate side 116a and a distal side 116b) to image the sensing region 111 under a limited field of view. The aperture 116 is coupled with a structure 117 having a proximate side 117a and a distal side 117b. Located adjacent to portions of the distal side 116b of the aperture 116 and the distal side 117b of the structure 117 are a first peripheral prism 118a (or other such diverter) and a second peripheral prism 118b.

The enhanced detection system 100 includes a first peripheral detector 120a (e.g. photomultiplier tube), and a second peripheral detector 120b located to receive light transmitted through the first peripheral prism 118a and the second peripheral prism 118b, respectively. The enhanced detection system 100 further includes a first parametric characteristics detector 122 and a second parametric characteristics detector 124 each receiving light of different wavelengths according to a second dichroic mirror 126. In aggregate, these components provide cytometric information about cells passing through the sensing region by measuring the scattered light and fluorescence at two (or more) different excitation wavelengths. By adding more apertures, the functionality of the sensor can be extended by adding a number of laser lines to excite other fluorophores.

When a particle in the sensing region 111 is in-focus, light from the first laser 102 and the second laser 104 will be directed straight through the aperture 116 so that substantially only the first parametric characteristics detector 122 and the second parametric characteristics detector 124 will sense the light as shown in FIG. 1.

The enhanced detection system 100 is also shown to include a CCD camera 128 that allows visualization of both the sensing region 111 and laser illumination for such things as alignment. Additionally, the CCD camera 128 gives the option of imaging larger particles.

Figure 2:
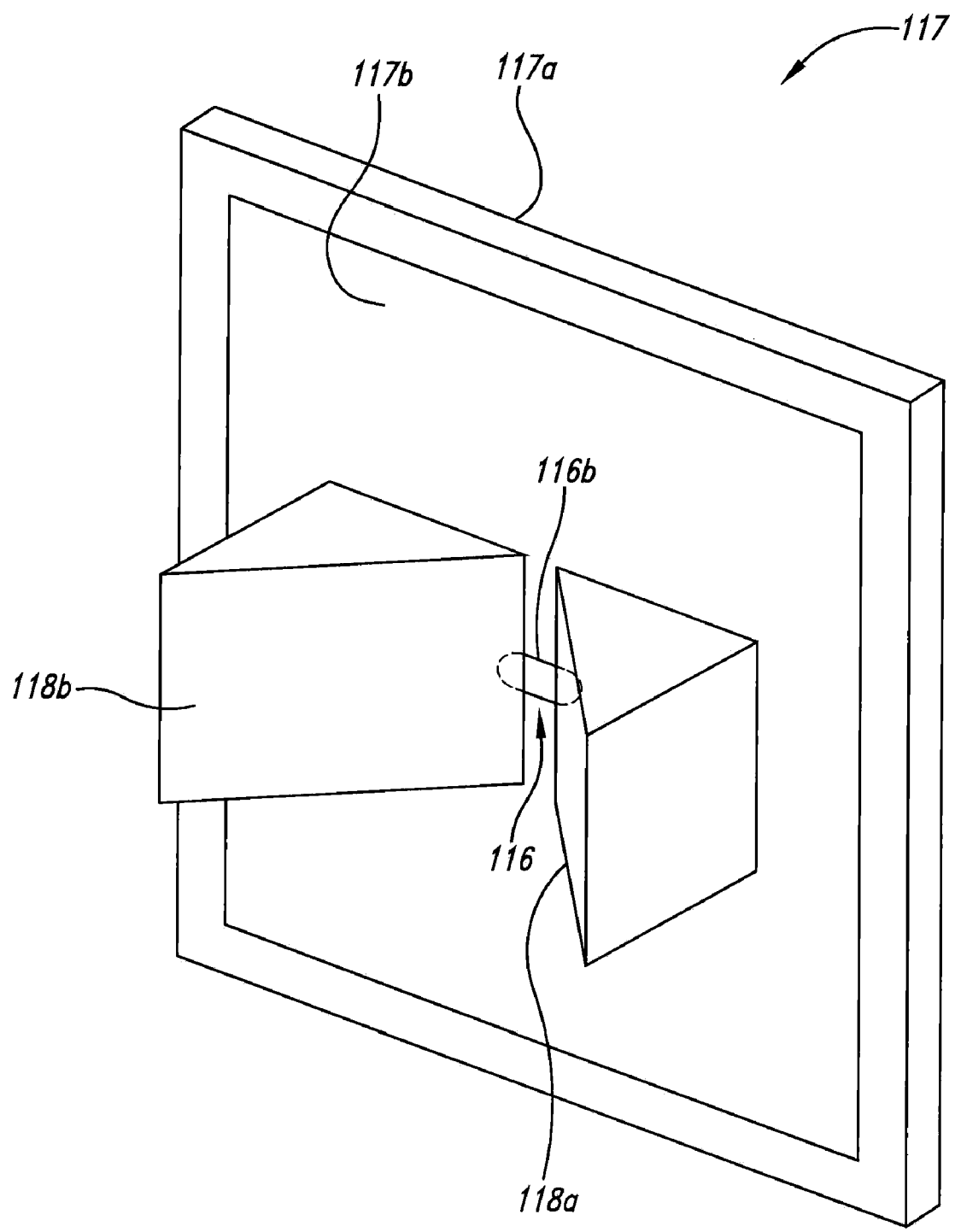
FIG. 2 is a perspective view of a portion of the detection system of FIG. 1.

The aperture 116, the structure 117, the first peripheral prism 118a, and the second peripheral prism 118b are shown in FIG. 2 in an enlarged view. The depicted implementation includes the aperture 116 as elongated with portions of the first peripheral prism 118a and the second peripheral prism 118b located adjacent to end portions of the aperture. Light from a properly focused particle passes through the aperture 116 and on to the first parametric characteristics detector 122 and the second parametric characteristics detector 124.

Light from particles that are out-of-focus and therefore out of the focal area is cast onto the first peripheral prism 118a and the second peripheral prism 118b that overhang each end edge of the elongated dimension of the aperture 116 to be directed to the first peripheral detector 120a and the second peripheral detector 120b, respectively. Signals generated by the first peripheral detector 120a and the second peripheral detector 120b can be used by the controller 130 gate out measurements made by the first parametric characteristics detector 122 and the second parametric characteristics detector 124 related to particles that were out-of-focus while in the sensing region 111.

As discussed above, as shown in FIG. 3A, when light is directed straight through the aperture 116, it is received by the first parametric characteristics detector 122 (and the second parametric characteristics detector 124 if the second chronic mirror 126 is used). If light is directed through the aperture 116 on an angle due to a particle being located in an out-of-focus position in the sensing region 111, as shown in FIG. 3B, the light will be further directed to the first peripheral detector 120a through the first peripheral prism 118a and/or the second peripheral detector 120b through the second peripheral prism 120b.

Figure 4:
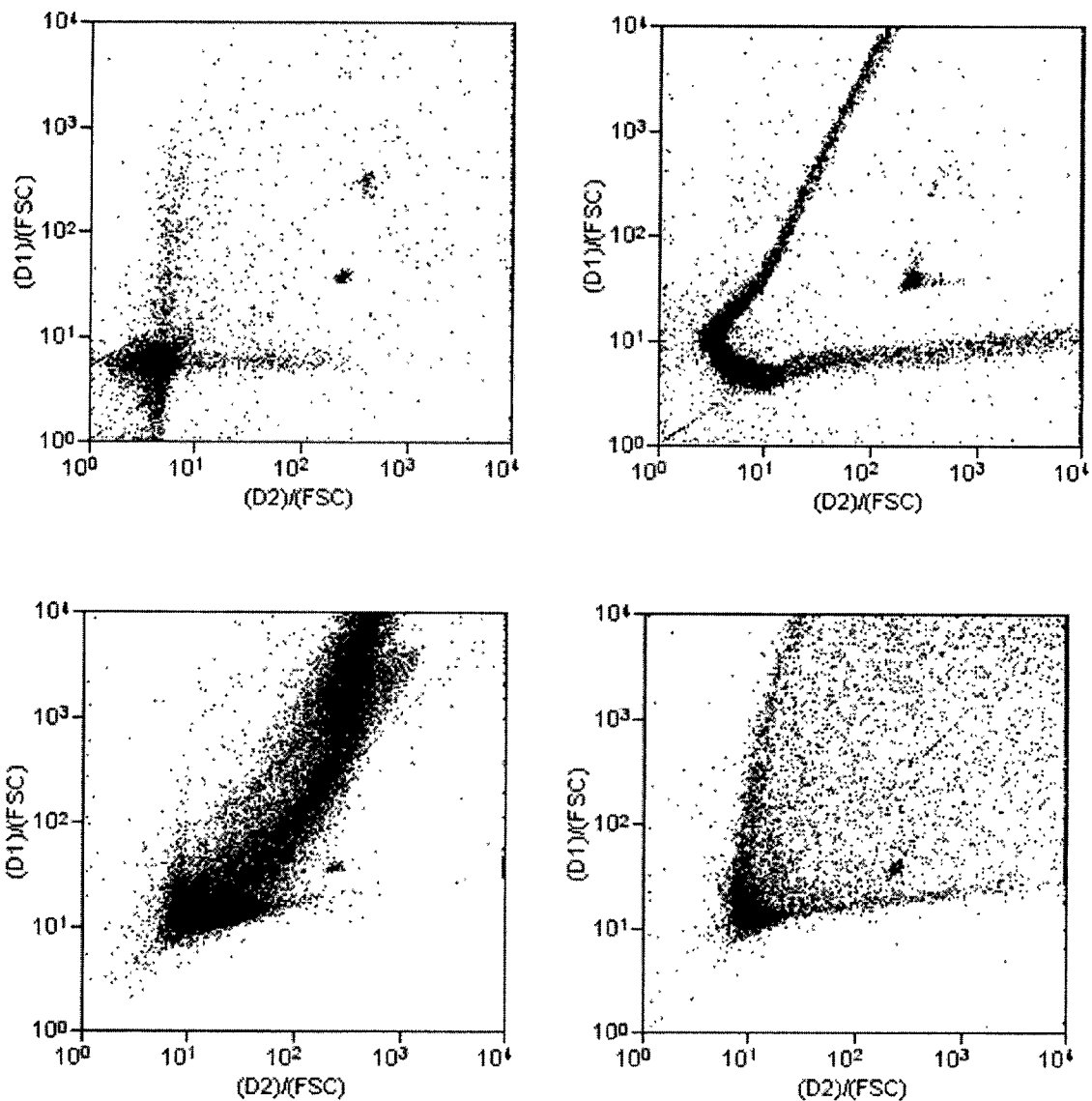
FIG. 4 is a first collection of plots showing detection results of an implementation of the enhanced detection system of FIG. 1.

Measurement results are shown in FIG. 4 for an implementation of the enhanced detection system 100 using a 488 nm or a 357 nm laser as the excitation source and the prism 108 to steer laser light through a 20× or 10× version of the objective 110. Scattered and fluorescent light emission from particles in a typical flow cytometer stream was collected using the enhanced detection system 100. Depicted measurements are for 1.0 □m polystyrene beads both in and out of the focal area. Out-of-focus particle measurements were simulated by moving the stream from side to side, as well as forwards and back. As illustrated in FIG. 4 clockwise from top left: no movement, side to side 0.001" each way, forward 0.001", and back 0.001". Fluorescent yellow-green 1.0 □m beads, 10× objective, 488 nm 200 mW excitation.

Figure 5:
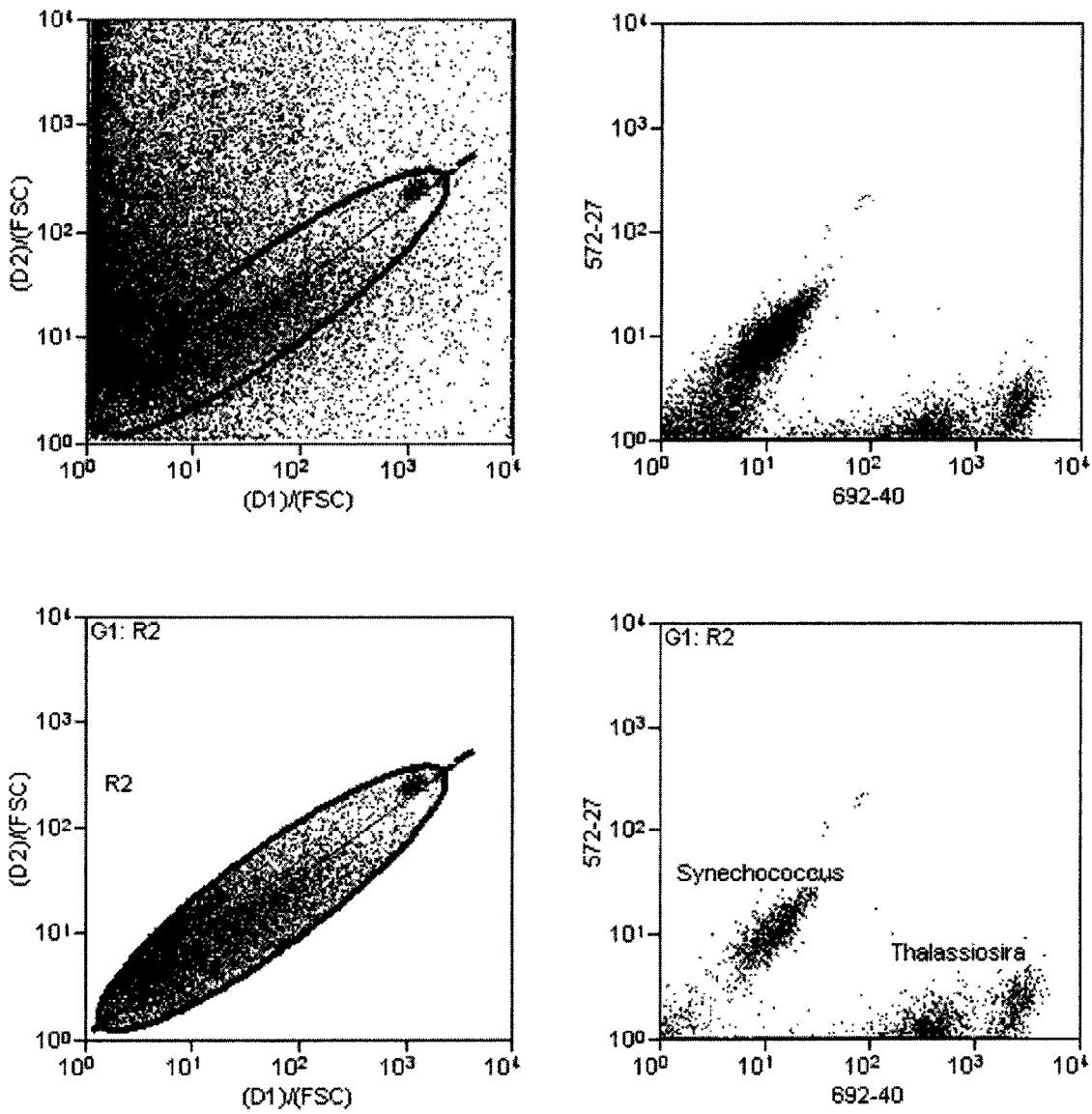
FIG. 5 is a second collection of plots showing detection results of an implementation of the enhanced detection system of FIG. 1.

Ability of the enhanced detector 100 to measure real cell populations is depicted in FIG. 5. A mix of marine algae was injected into a typical flow cytometer stream with the sample pressure boosted to a level where the sample flow was unsteady and not necessarily in the focal area of a 20× version of the objective 110. Light signals detected by the enhanced detection system 100 (the first peripheral detector 120a being labeled as D1 and the second peripheral detector 120b being labeled as D2) that are common to both peripheral detectors are in the side-side center of the sheath fluid. The proximal and distal position of a particle from the in-focus position can be determined from the relative levels of light that passes directly through the aperture 116 as sensed by the first parametric characteristics detector 122 and the second parametric characteristics detector 124 and the light that is cast onto the first peripheral prism 118a as sensed by the first peripheral detector 120a and the second peripheral prism 118b as sensed by the second peripheral detector 120b in this method for determining position of particle with respect to optimal focal area. Epi-illuminescent measurement (BSC) of *Synechococcus* spp., *Thalassiosira pseudonana*, and *Thalassiosira weisfloglii* marine algae are shown; 300 mW 457 nm excitation, 20× objective. The gated region at the left is used to filter out events from particles that are not properly positioned for a measurement. Gated data showing chlorophyll versus phycoerythrin are shown at bottom right.

It will be readily understood by those persons skilled in the art that the present invention is susceptible of broad utility and application. Many embodiments and adaptations of the present invention other than those herein described, as well as many variations, modifications and equivalent arrangements, will be apparent from or reasonably suggested by the present invention and the foregoing description thereof, without departing from the substance or scope of the present invention. Accordingly, while the present invention has been described herein in detail in relation to its preferred embodiments, it is to be understood that this disclosure is only illustrative and exemplary of the present invention and is made merely for purposes of providing a full and enabling disclosure of the invention. The foregoing disclosure is not intended or to be construed to limit the present invention or otherwise to exclude any such other embodiments, adaptations, variations, modifications and equivalent arrangements, the present invention being limited only by the claims filed and the equivalents thereof.

The invention claimed is:

1. A system for analyzing particles in a flow stream, comprising:
   an objective configured to direct light from a sensing region within said flow stream, the sensing region including an in-focus position, to an aperture having a proximate side and a distal side, the proximate side being closer to the objective than the distal side, wherein said aperture is elongated and has a center region, a first side region adjacent to one edge of the elongated dimension, and a second side region adjacent to an edge of the elongated dimension, opposite said first side region;
   a lens configured to focus said light directed by said objective from said in-focus position within said sensing region onto said aperture,
   a first peripheral diverter positioned to receive light from said first side region of said aperture, and a first peripheral detector configured to receive light transmitted through said first peripheral diverter;
   a second peripheral diverter positioned to receive light from said second side region of said aperture, and a second peripheral detector configured to receive light transmitted through said second peripheral diverter; and
   a first parametric characteristics detector positioned to receive light from said center region of said aperture;
   wherein said elongated dimension of said aperture is oriented such that light emitted from said sensing region that is outside of said in-focus region in a sideways direction relative to the direction of the flow stream will be directed to one of said peripheral prisms.

2. The system of claim 1, further comprising a controller configured to receive signals from said first peripheral detector, said second peripheral detector, and said first parametric characteristics detector.

3. The system of claim 1, wherein the said first and second peripheral diverters are prisms.

4. The system of claim 1, wherein the first and second peripheral detectors are photomultiplier tubes.

5. The system of claim 1, further comprising a second parametric characteristics detector positioned to receive light from said center region of said aperture, wherein said first and said second parametric characteristics detectors receive light of different wavelengths.

* * * * *